US007282333B2

(12) United States Patent
Brow et al.

(10) Patent No.: US 7,282,333 B2
(45) Date of Patent: Oct. 16, 2007

(54) METHODS AND COMPOSITIONS FOR NUCLEIC ACID ANALYSIS

(75) Inventors: Mary Ann Brow, Madison, WI (US); David A. Casimir, Verona, WI (US)

(73) Assignee: Promega Corporation, Madison, WI (US)

( * ) Notice: Subject to any disclaimer, the term of this patent is extended or adjusted under 35 U.S.C. 154(b) by 376 days.

(21) Appl. No.: 10/969,032

(22) Filed: Oct. 20, 2004

(65) Prior Publication Data

US 2005/0084894 A1  Apr. 21, 2005

Related U.S. Application Data

(60) Provisional application No. 60/512,638, filed on Oct. 20, 2003.

(51) Int. Cl.
*C12Q 1/68* (2006.01)
*C12P 19/34* (2006.01)
*C07H 19/00* (2006.01)
*C07H 21/02* (2006.01)
*C07H 21/04* (2006.01)

(52) U.S. Cl. .................. 435/6; 435/91.2; 536/22.1; 536/23.1; 536/24.3

(58) Field of Classification Search ............ 435/6, 435/91.2; 536/23.1, 24.3, 22.1
See application file for complete search history.

(56) References Cited

U.S. PATENT DOCUMENTS

| 5,216,141 | A | 6/1993 | Benner |
| 5,432,272 | A | 7/1995 | Benner |
| 5,565,340 | A | 10/1996 | Chenchik et al. |
| 5,912,340 | A | 6/1999 | IKutyavin et al. |
| 5,958,702 | A | 9/1999 | Benner |
| 5,965,364 | A | 10/1999 | Benner |
| 6,001,983 | A | 12/1999 | Benner |
| 6,037,120 | A | 3/2000 | Benner |
| 6,140,496 | A | 10/2000 | Benner |
| 6,270,967 | B1 | 8/2001 | Whitcombe et al. |
| 7,056,703 | B2 * | 6/2006 | Callen et al. .................. 435/6 |
| 2002/0150900 | A1 | 10/2002 | Marshall et al. |
| 2004/0106108 | A1 | 6/2004 | Grenier et al. |

OTHER PUBLICATIONS

Newton et al., The Production of PCR Products with 5' Single-Stranded Tails Using Primers That Incorporate Novel Phosphoramidite Intermediates. Nucleic Acids Res 21:1155-1162 (1993).*
ABI Prism Dye Terminator Cycle Sequencing Core Kit with AmpliTaq DNA Polymerase, FS : Protocol published by Applied Biosystems (Copyright 2001).*
U.S. Appl. No. 09/415,966, filed Oct. 12, 1999, Benner.
U.S. Appl. No. 09/538,338, filed Mar. 29, 2000, Benner.
U.S. Appl. No. 09/993,757, filed Nov. 27, 2001, Thorson.
U.S. Appl. No. 60/205,712, filed May 19, 2000, Marshall.
U.S. Appl. No. 60/240,398, filed Oct. 14, 2000, Marshall.
U.S. Appl. No. 60/282,831, filed Apr. 10, 2001, Marshall.
U.S. Appl. No. 60/240,397, filed Oct. 14, 2000, Grenier.
U.S. Appl. No. 60/252,783, filed Nov. 22, 2000, Prudent et al.
U.S. Appl. No. 60/253,382, filed Nov. 27, 2000, Thorson.
Allawi, H.T. & SantaLucia, J. Jr. Thermodynamics of Internal G-T Mismatches, Biochemistry 36(34):10581-94 (1997).
Lin, PKT. and Brown,D.M., Synthesis and duplex stability of oligonucleotides containing cytosine-thymine analogues. Nucleic Acids Res. 17 10373-10383 (1989).
Lin, PKT. and Brown,D.M., Synthesis of oligodeoxyribonucleotides containing degenerate bases and their use as primers in the polymerase chain reaction, Nucleic Acids Res. 20 (19):5149-52 (1992).
Brownie, et al., "The elimination of primer-dimer accumulation in PCR," Nucleic Acids Res. 25(16): 3235-41 (1997).
Robinson, H., et al., 2'-Deoxyisoguanosine Adopts More Than One Tautomer To Form Base Pairs With Thymidine Observed by High-Resolution Crystal Structure Analysis, Biochemistry Aug. 4, 1998;37(31):10897-905.
Switzer, CY, et al., Enzymatic Recognition of the Base Pair Between Isocytidine and Isoguanosine, Biochemistry Oct. 5, 1993;32(39):10489-96).
Roberts, C., et al., Synthesis of Oligonucleotides Bearing the Non-Standard Bases IsoOC and Iso-G. Comparison of iso-C-isoG, C-G, and U-A Base-Pair Stabilities in RNA/DNA Duplexes, Tetrahedron Letters 36 (21):3601-3604 (1995).
McMinn, DL, et al., Efforts toward the Expansion of the Genetic Alphabet: DNA Polymerase Recognition of a Highly Stable, Self-Pairing Hydrophobic Base, J. Am Chem. Soc. 121:11585-11586 (1999).
Moran, S., et al., Difluorotoluene, a Nonpolar Isotere for Thymine, Codes Specifically and Efficiently for Adenine in DNA Replication, J. Am Chem. Soc. 119:2056-2057 (1997).
Moser, MJ, et al., Exploiting the Enzymatic Recognition of an Unnatural Base Pair to Develop a Universal Genetic Analysis System, Clinical Chemistry 49(3):407-414 (2003.
Ren, R X -F., et al., Naphthalene, Phenanthrese, and Pyrine as DNA Base Analogs: Synthesis, Structure, and Fluorescence in DNA, J. Am Chem. Soc. 118:7671-7678 (1996).
Wilhelm J and A. Pingoud, Real Time Polymerase Chain Reaction, Chem BioChem 4:1120-1128 (2003).
Rice, KP, et al., RecA Protein Promotes Strand Exchange with DNA Substrates Containing Isoguanine and 5-Methyl Isocytosine, Biochemistry 39:10177-10188 (2000).

(Continued)

*Primary Examiner*—Ethan Whisenant
(74) *Attorney, Agent, or Firm*—Medlen & Carroll, LLP

(57) ABSTRACT

The present invention relates to improved methods and composition for nucleic acid analysis. In particular, the present invention provides improved methods and compositions for carrying out nucleic acid analysis using modified nucleotides.

37 Claims, 4 Drawing Sheets

OTHER PUBLICATIONS

Kool, E., "Synthetically modified DNAs as substrates for polymerases," Current Opinions in Chemical Biology 2000 4:802-808.

Kainz et al., "Specificity-Enhanced Hot-Start PCR: Addition of Double-Stranded DNA Fragments Adapted to the Annealing Temperature," BioTechniques 28:278.

Kamiya et al., "Formation of 2-Hydroxydeoxyadenosine Triphosphate, an oxidatively Damaged Nucleotide, and Its Incorporation by DNA Polymerases," J. of Biol. Chem 270:19446-194.

Whitcomb et al., "A homogeneous fluorescence assay for PCR amplicons: its application to real-time, single-tube genotyping," Clinical Chemistry 44:918-923 (1998).

* cited by examiner

FIGURE 2
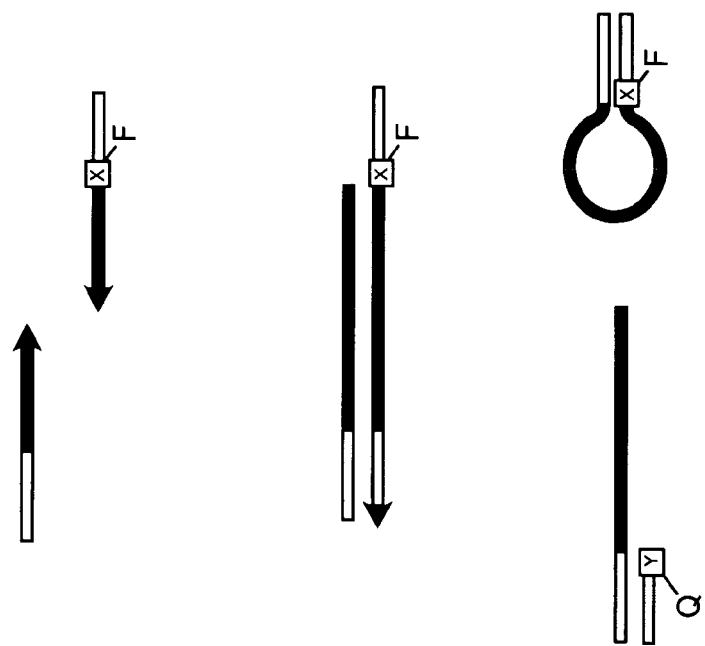
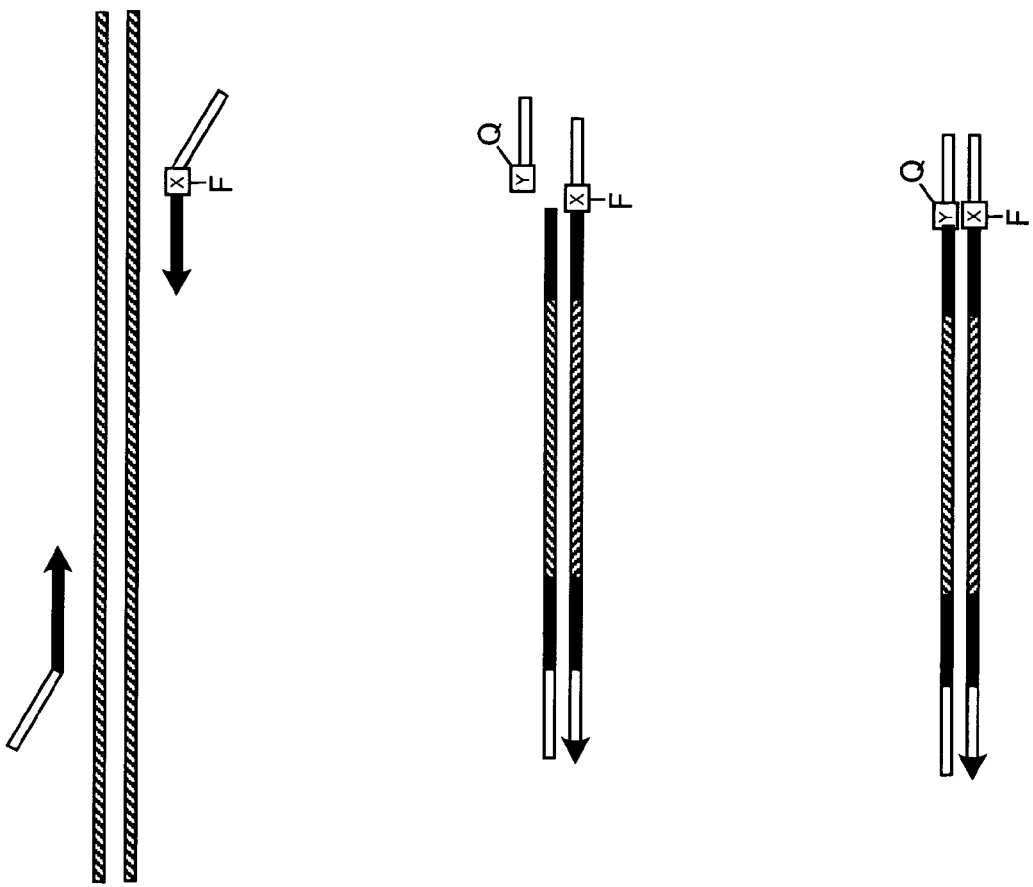

METHODS AND COMPOSITIONS FOR NUCLEIC ACID ANALYSIS

The present Application claims priority to Provisional Application Ser. No. 60/512,638, filed Oct. 20, 2003, which is incorporated herein by reference in its entirety.

FIELD OF THE INVENTION

The present invention relates to improved methods and composition for nucleic acid analysis. In particular, the present invention provides improved methods and compositions for carrying out nucleic acid analysis using modified nucleotides.

BACKGROUND OF THE INVENTION

The development and use of modified nucleotides has expanded the range of nucleic acid analysis techniques. For example, the modified non-natural nucleotides of Eragen Corporation expand the alphabet of bases that may be used in nucleic acid technologies (See e.g., U.S. Pat. Nos. 5,216,141, 5,432,272, 5,958,702, 5,965,364, 6,001,983, 6,037,120, and 6,140,496 and patent application Ser. Nos. 09/415,966, 09/538,338, 09/993,757, 60/205,712, 60/240,398, 60/282,831, 60/240,397, 60/252,783, and 60/253,382, each of which is incorporated herein in its entirety). While these modified nucleotides have been found useful, compositions and methods that provide improved sensitivity and flexibility in using such products in nucleic acid analysis methods are needed.

Modified nucleotides also find use in nucleic acid amplification reactions such as the polymerase chain reaction. See, e.g., U.S. Ser. No. 09/861,292, published as Publication No. 2002/0150900, and U.S. Ser. No. 10/977,615, published as Publication No. 2004/0106108, each of which is incorporated herein by reference in its entirety. While these applications have been found useful, methods and compositions that reduce background signal and improve assay sensitivity are needed.

SUMMARY OF THE INVENTION

The present invention relates to improved methods and compositions for nucleic acid analysis. In particular, the present invention provides improved methods and compositions for carrying out nucleic acid analysis using modified nucleotides. Still more particularly, the present invention provides improved methods and compositions for carrying out nucleic acid analysis using non-naturally occurring nucleotides that are complementary to other non-naturally occurring nucleotides but that are capable of base-pairing to one or more naturally occurring nucleotides.

In some embodiments, the present invention provides a kit comprising an extension-disabled non-naturally occurring nucleotide. In some preferred embodiments, the kit further comprises one or more of an oligonucleotide primer, a polymerase (e.g., a DNA polymerase, a thermostable polymerase, a polymerase lacking 5' nuclease activity, etc.), and reagents for conducting a polymerase chain reaction. In some preferred embodiments, the extension-disabled non-naturally occurring nucleotide comprises a dideoxy nucleotide (e.g., a dideoxy iso-G).

The present invention further provides methods for analyzing a target nucleic acid, comprising: exposing a target nucleic acid to polymerase, a first amplification primer having a first non-natural nucleotide, a second amplification primer, and an extension-disabled second non-natural nucleotide complementary to said first non-natural nucleotide under conditions such that an extension product is generated from at least said second amplification primer, wherein said extension product incorporates said second non-natural nucleotides. In some embodiments, the first and second amplification primers are selected to hybridize to a portion of said target nucleic acid to define an amplification region, wherein said amplification region is selected to minimize the presence of T nucleotides in said amplification region.

In some embodiments, the present invention provides improved methods of performing primer-directed amplification reactions, such as PCR. In some embodiments, the present invention provides methods and compositions for reducing signal from background amplification products, particularly primer-dimer amplification products. In some embodiments, the reduction of signal from primer-dimer products comprises use of primers having a tag sequence. When each of the target-specific primers for PCR amplification comprises the same tag sequence, each of the strands of the resulting amplicons will comprise self-complementary portion (i.e., the tag from the primer at or near the 5' end, and the complement of the tag sequence at or near the 3' end. For long products, single-stranded portion of the adapters at each end of the ssDNA fragment may form either a self-annealing "panhandle-like" structure (amplification suppressive structure) or a DNA/primer "hybrid" structure (amplification permissive structure). The relative ratio of formation of the two structures using the subject method during PCR cycling depends on a number of factors, including the differences between the melting temperatures of the suppressive and permissive structures, the position of the complementary primer binding site within the adapter sequence, and the size of the DNA fragment to be amplified. These factors can be manipulated to achieve the desired suppression of non-target DNA during PCR amplification. In some embodiments, the formation of panhandle structures in primer-dimer products separates interactive labels, so as to reduce or eliminate detection of primer-dimer products formed in the reaction.

In some embodiments the present invention comprises a method for detecting a target nucleic acid, comprising: a) contacting the sample with a polymerase; a first oligonucleotide primer comprising a 3' region complementary to a first portion of the target nucleic acid and a 5' region comprising a tag sequence; a second oligonucleotide primer comprising a 3' region comprising a sequence complementary to a second portion of the target nucleic acid, a 5' region comprising the tag sequence, and a 5' terminal region comprising a non-natural base; b) conducting a polymerase chain reaction to produce an amplified sample under conditions wherein the target nucleic acid, if present in the sample, is amplified using the first and second oligonucleotide primers to generate amplification products comprising a target amplification product having (i) a double-stranded region and (ii) a single-stranded region that comprises the non-natural base, c) contacting said amplified sample with a reporter comprising a label and a non-natural base that is complementary to the non-natural base of the single-stranded region; d) incorporating the reporter into the amplification product opposite the non-natural base of the single-stranded region; and e) detecting the incorporation of the reporter; wherein the detection of the incorporation of the reporter correlates with presence of the target nucleic acid in the sample. In some embodiments, the method further comprises the step e) of treating the amplified sample under conditions wherein non-target amplification product consisting essentially of primer-dimer product is treated to separate the strands, wherein each separated strand forms a duplex region comprising a tag sequence and a region that is complementary to the tag sequence.

In some embodiments, each of the second oligonucleotide primer and said reporter comprise interactive labels. In some preferred embodiments, the interactive labels comprise a fluorophore. In some embodiments, said interactive labels comprise a quencher.

In some embodiments, the step of contacting the sample with a reporter comprises contacting the sample with a reporter comprising a label and a nucleoside triphosphate of a non-natural base that is complementary to the non-natural base of the single-stranded region. In some embodiments, the step of contacting the sample with a reporter comprises contacting the sample with a reporter consisting essentially of a label and a nucleoside triphosphate of a non-natural base that is complementary to the non-natural base of the single-stranded region.

In some embodiments, the incorporating step comprises incorporating the reporter into the amplification product opposite the non-natural base of the single-stranded region using a nucleic acid polymerase. In other embodiments, the incorporating step comprises incorporating the reporter into the amplification product opposite the non-natural base of the single-stranded region using a ligase.

In some embodiments, the present invention comprises a kit comprising: a first oligonucleotide primer comprising a 3' region complementary to a first portion of the target nucleic acid and a 5' region comprising a tag sequence, a second oligonucleotide primer comprising a 3' region comprising a sequence complementary to a second portion of the target nucleic acid, a 5' region comprising the tag sequence, and a 5' terminal region comprising a non-natural base; and a reporter comprising a label and a non-natural base that is complementary to the non-natural base in said second oligonucleotide primer. In some embodiments the kit further comprises a third oligonucleotide primer comprising a 3' portion consisting essentially of said tag sequence.

In some embodiments of the kits of the present invention, the reporter comprises an oligonucleotide comprising the non-natural base. In some embodiments, the reporter does not include any base other than the non-natural base.

In some embodiments, the second region of the second oligonucleotide primer further comprises a label and the labels of the reporter and the second region of the second oligonucleotide primer comprise a pair of fluorophores where the emission of one of the fluorophores stimulates the emission of the other fluorophore.

In some embodiments, the second region of the second oligonucleotide primer further comprises a label and the labels of the reporter and the second region of the second oligonucleotide primer comprise a signal generating element and a signal quenching element.

Definitions

To facilitate an understanding of the present invention, a number of terms and phrases are defined below:

As used herein, the terms "subject" and "patient" refer to any organism, including a plant, a microorganism or an animal (e.g., a mammal such as a dog, cat, livestock, or human, or a non-mammal, such as a bird, an amphibian or a fish).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

In some situations, a label comprises two or more interactive labels, either on a single oligonucleotide, or on different strands of an nucleic acid duplex or other complex (e.g., triplex or quartet). One type of interactive label pair is a quencher-dye pair. Preferably, the quencher-dye pair comprises a fluorophore and a quencher. Suitable fluorophores include, for example, fluorescein, cascade blue, hexachloro-fluorescein, tetrachloro-fluorescein, TAMRA, ROX, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaz-a-S-indacene-propionic acid, 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a, 4a-diaza-s-indacene 3-propionic acid and 4,4-difluoro-5-styryl-4-bora-3a,4a-diaza-S-indacene-ptopionic acid. Suitable quenchers include, for example, Dabcyl, QSY7 (Molecular Probes, Eugene, Oreg.) and the like. In some embodiments, dyes (e.g., fluorphores or chromophores) can also be used as a quencher (e.g., if they absorb the emitted light of another dye).

As used herein the term "interactive label" refers to a label having two or more components that interact so as to produce a detectable effect. The interaction is not limited to any particular nature of interaction. The interaction of the label components may be via direct contact, e.g., a covalent or non-covalent contact between two moieties (e.g., a protein-protein contact, or collisional energy transfer between proximal moieties); it may comprise resonance energy transfer (e.g., between one or more dyes, or between a dye and a quencher moieties); it may comprise a diffusion effect, e.g., wherein the product from a reaction occurring at the site of one label diffuses to the site of another label to create a detectable effect. The components of an interactive label may be the same (e.g., two or more of the same molecule or atom) or they may be different.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \ G+C)$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "thermostable" when used in reference to an enzyme, such as a 5' nuclease, indicates that the enzyme is functional or active (i.e., can perform catalysis) at an elevated temperature, i.e., at about 55° C. or higher.

The term "target nucleic acid" refers to a nucleic acid molecule containing a sequence that has at least partial complementarity with at least a probe or primer sequence. The target nucleic acid may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "$K_m$" as used herein refers to the Michaelis-Menten constant for an enzyme and is defined as the concentration of the specific substrate at which a given enzyme yields half its maximum velocity in an enzyme catalyzed reaction.

The term "natural" as used herein to describe nucleotides and bases refers to the most common components of DNA and RNA nucleic acid, i.e., A, C, G, T and U nucleotides.

The term "nucleotide analog", "non-natural", or "non-naturally occurring" as used herein refers to nucleotides other than the natural nucleotides and bases. Such analogs and non-natural bases and nucleotides include modified natural nucleotides and non-naturally occurring nucleotides, including but not limited to analogs that have altered stacking interactions such as 7-deaza purines (i.e., 7-deaza-dATP and 7-deaza-dGTP); base analogs with alternative hydrogen bonding configurations (e.g., such as iso-C and iso-G and other non-standard base pairs described in U.S. Pat. No. 6,001,983 to S. Benner, and the selectively binding base analogs described in U.S. Pat. No. 5,912,340 to Igor V. Kutyavin, et al.); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include modified forms of deoxyribonucleotides as well as ribonucleotides. "Non-natural" and "non-naturally occurring" bases and nucleotides are specifically not limited to such bases as are never found in nature. Natural processes such as nucleic acid damage can give rise to "natural" occurrence of bases that are nonetheless not generally considered to be part of the set of "natural" nucleotides as defined herein. For example, iso-G can be found in oxidatively damaged DNA. Such non-natural bases and their behaviors in replication and other nucleic acid syntheses have been extensively studied in contexts such as DNA damage studies, although the compounds are sometimes described using different nomenclature. For example, the ribonucleoside comprising the isoguanosine base has been referred to in the literature variously as: iG; isoG; iso-G; isoguanosine; 2-hydroxyadenine; 2-oxoadenine; 2-hydroxy A; and 2-OH-A. The deoxyribonucleoside comprising the isoguanosine base has been referred to variously as: iG; isoG; iso dG; deoxyiso-G; deoxyisoguanosine; 2-hydroxydeoxyadenosine; 2-hydroxy dA; and 2-OH-Ade.

The prefix "dideoxy" as use herein to describe a nucleotide (e.g., dideoxyisoguanosine triphosphate, dideoxy G), refers to a nucleotide lacking hydroxyl group at both the 2' and 3' positions of the sugar moiety (e.g., the ribose in a natural nucleotide). The prefix is not intended to indicate the absence of any other particular group at such positions, and the sugar may comprise other moieties at one or both positions.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism that is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

The term "nucleic acid sequence" as used herein refers to an oligonucleotide, nucleotide or polynucleotide, and fragments or portions thereof, and to DNA or RNA of genomic or synthetic origin which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF DRAWINGS

FIG. 2 shows a schematic diagram of one embodiment of the present invention.

DETAILED DESCRIPTION OF THE INVENTION

Figure 1:
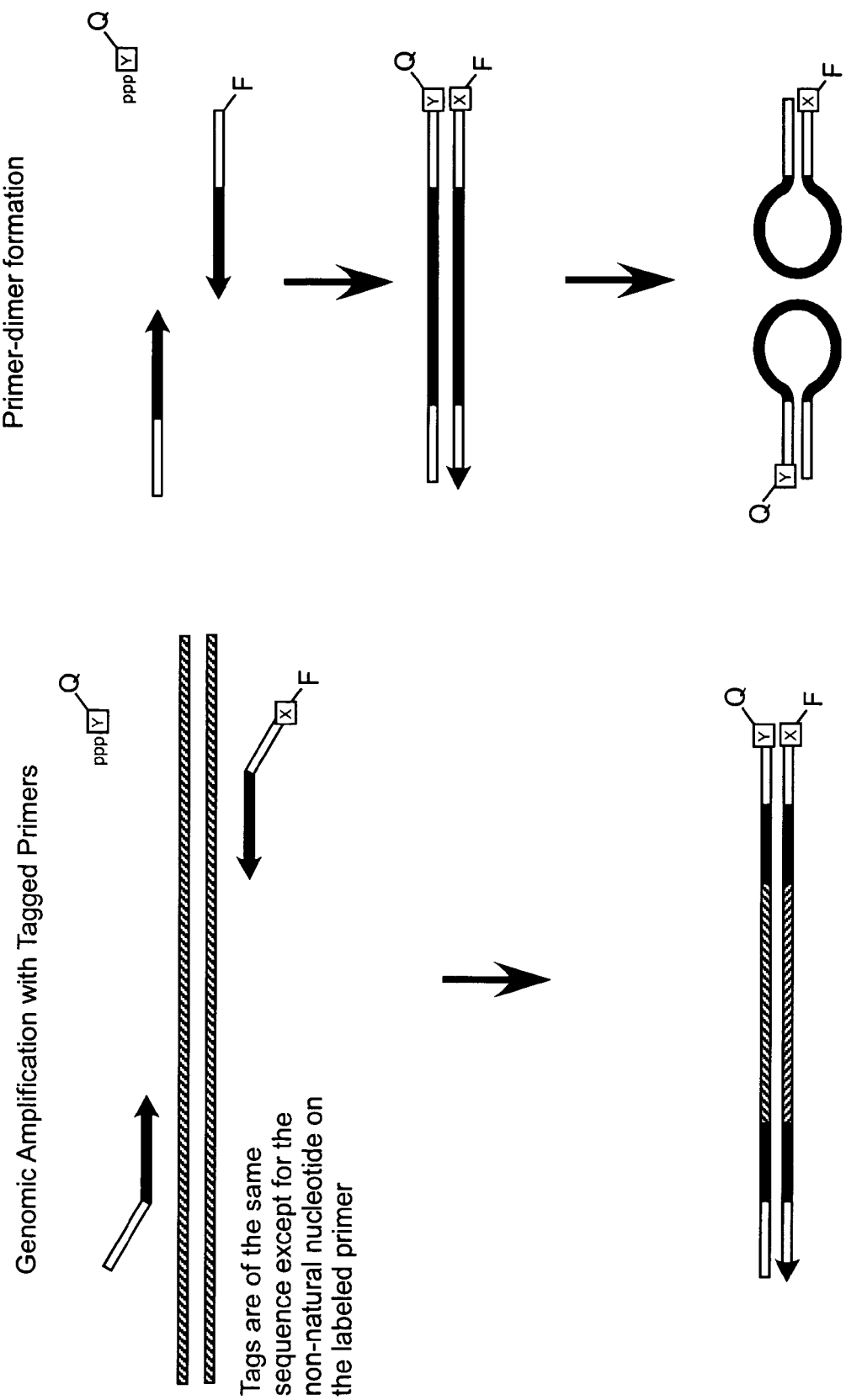
FIG. 1 shows a schematic diagram of one embodiment of the present invention.

The present invention relates to improved methods and composition for nucleic acid analysis. In particular, the present invention provides improved methods and compositions for carrying out nucleic acid analysis using modified nucleotides.

In some embodiments, the present invention provides extension-disabled non-naturally occurring nucleotides for use in nucleic acid analysis technologies. "Extension-disabled" refers to nucleotides that are modified to substantially reduce or eliminate the ability of a polymerase to extend a growing nucleic acid chain once the extension-disabled nucleotide has been added. In some embodiments, the extension disabled non-naturally occurring nucleotide is a dideoxy non-naturally occurring nucleotide.

Nucleic acid methods, such as the GENECODE methods of Eragen Corporation employ complementary non-naturally occurring nucleotides such as iso-G and iso-C to expand the alphabet of the genetic code for nucleic acid analysis. In these methods, a non-naturally occurring nucleotide is present in a primer. When the primer is extended in, for example, a polymerase chain reaction, the non-natural base becomes incorporated into one strand of the amplification products. When this strand is used as a template in a subsequent amplification step, Eragen reports that the natural bases will not incorporate across from the non-natural base. This failure to incorporate is used as a point of discrimination in some GENECODE methods (e.g., by allowing only labeled, complementary non-natural bases to be added).

In some embodiments, a nucleoside triphosphate comprising a second non-naturally occurring base is included in amplifications in which a first non-naturally occurring base is used in a primer. The second non-naturally occurring base is selected to be complementary to the first non-naturally occurring base. When the strand comprising the primer is used as a template in a subsequent amplification step, the second non-naturally occurring base is incorporated into the new strand only where the first non-naturally occurring base is present in the template. This selective incorporation is used as a point of discrimination in some GENECODE methods (e.g., by allowing labeled, complementary non-natural bases to be added only where a template strand comprises a non-natural base).

However, the GENECODE literature does not appreciate a problem with such methods. Non-natural bases such as iso-G, which are used in the GENECODE technologies, are capable of forming base pairs with natural bases. For example, iso-G will basepair with T and U. At low temperatures, e.g., 2° C., basepairs between iso-G and T have been shown to be predominantly are in the wobble form. As the temperature of a reaction is increased (i.e., as occurs in a polymerase chain reaction), another form or iso-G, the enol form, becomes significantly populated. This form of iso-G pairs with T in a Watson-Crick configuration to a significant extent at physiological temperature (37° C.). (H. Robinson, et al., Biochemistry 1998 Aug. 4;37(31):10897-905). Consequently, iso-G and T can serve as complementary bases in DNA replication reactions. For example, a number of DNA polymerases have been shown to catalyze the template-directed formation of a base pair between (iso-G and T). In a template, iso-G directs the incorporation of both iso-C and T when Klenow fragment is the catalyst. Some polymerases will preferentially incorporate a natural base as a complement of iso-G. For example, T7 RNA polymerase will incorporate only U as a complement to iso-G in RNA synthesis, even when iso-CTP is present in the reaction. (C. Switzer, et al., Biochemistry 1993 Oct. 5;32(39):10489-96).

Where labeled iso-G bases are inadvertently incorporated (e.g., as a complement to T or U residues in a template strand) background signal in methods such as the GENECODE method increases. The present invention provides compositions and methods for avoiding this problem.

In one preferred method, an extension-disabled non-naturally occurring nucleotides is used in the reaction. In such methods, the only complete amplicons created in a chain extension reaction (e.g., a GENECODE reaction) will be those that avoid the undesired incorporation of the non-naturally occurring nucleotides.

In some embodiments, the accumulation of PCR product may be monitored by quenching the signal of a label on the second primer by site-specific incorporation of a nucleotide triphosphate across the DNA duplex at a position near the label of the second primer. The labeled nucleoside triphosphate is incorporated into the elongating first primer during PCR extension. The label on the labeled nucleoside triphosphate is capable of quenching the label on the second primer. In an alternative embodiment, fluorescence energy transfer (FRET) can be observed between the label of the second primer (donor dye) and a label on the nucleotide (acceptor dye). Detection of PCR product can be observed by exciting the donor dye and reading the emission of the incorporated acceptor dye.

In design of these systems it is preferred that the labeled nucleoside triphosphate is complementary to a nucleotide near the label of the primer. When using a naturally occurring nucleotide base that is labeled, the ability to selectively incorporate such a complementary base only near the label of the primer is possible only in a limited number of cases. This is because all four naturally occurring nucleotide bases are likely to be incorporated at other positions during amplification of a target sequence. By using labeled non-natural bases, e.g., labeled iso-G and iso-C, the likelihood of incorporating a labeled base only opposite a complimentary non-natural base is increased. However, as described above, some non-naturally occurring bases basepair not only to a non-naturally occurring complement (e.g., iso-G to iso-C), but also basepair and are incorporated opposite one or more natural bases (e.g., iso-G and T). In some embodiments, it is desirable to control further extension of strands after the incorporation of such a labeled base, e.g., by using a labeled, extension-disabled non-naturally occurring nucleotide. Thus, when a labeled non-natural base is incorporated opposite a natural base, the chain is terminated. Such termination products can be later distinguished from the full-length intended products by virtue of size, or of differences in fluorescence characteristics (i.e., the incorporated label will be at a different distance from the primer label and will have different characteristics of quenching and/or energy transfer).

In some embodiments, PCR amplification products containing fluorophores quenched by site-specific incorporation of a quenching compound are subjected to melt curve analysis, e.g., in an instrument that can monitor fluorescence differences during temperature changes. The change in fluorescence is monitored while gradually increasing the temperature of the PCR reaction products (e.g., at a rate of 0.1.degree. C. per second). The Tm of the intended product (quencher-incorporated PCR product) as well as that of any nonspecific product (e.g., quencher-incorporated products that have been chain-terminated prematurely using the extension-disabled non-natural nucleotides of the present invention, or quencher-incorporated primer/dimers) may thus be determined. If the Tm of the intended product is selected to be substantially higher than the Tm of primer/dimers and the terminated products, the signal generated by the intended product may be specifically observed (and thus the presence or absence, or the quantity of the initial target material may be determined) by taking the fluorescent measurement of the reaction at a temperature above the Tm of the nonspecific products.

In some embodiments, incorporation of a non-natural base opposite a natural base is reduced by selection of a target region of particular sequence. For example, in some embodiments, the region that is amplified is selected to reduce or eliminate the presence of a natural base pair to the non-naturally occurring base (e.g., T-containing region in the target are avoided or reduced if labeled iso-GTP is used in the amplification reaction). This technique can be used alone, or in combination with the extension disabled non-naturally occurring nucleotides methods described above.

In some such embodiments, the selection of target sequences is carried out by "eye"—i.e., a user manually scans the target sequence to select a region with the desired sequence (e.g., one that contains no "T"s or is low in "T"s or has "T"s positioned such that they are less detrimental to the signal detection). In other embodiments, a processor is used to identify preferred target sequence by, for example, assessing the presence of, amount or, and/or location of bases to be avoided. The processor may further take into account other factors in selecting target regions. For example, the presence of undesired bases may be assessed in combination with hybridization characteristics, secondary structure, intellectual property considerations (e.g., the avoidance of particular sequences that are patented by others) etc.

Thus, the present invention provides systems and methods for applying target sequence information to a processor, parsing the sequence information with one or more algorithms, and generating one or more candidate target sequences. In some embodiments, the processor provides a report that provides estimated performance profiles of the assay to permit a user to select the appropriate target region or regions. In some embodiments, the algorithm identifies target regions by assessing one or more of: the presence of undesired bases, the location of undesired bases, the number of undesired bases, and the distance of undesired bases from the position of a detection moiety to be used in an assay (e.g., to reduce or eliminate undesired quenching or lack of quenching in a FRET assay by the undesired incorporation of a labeled non-natural nucleotide across from the undesired base).

Using the methods of the present invention, one is able to conduct techniques such as the GENECODE methods with longer amplicons (e.g., greater than 50 nucleotides, greater than 100, greater than 500, greater than 1000, greater than 2000, etc.), without incurring detrimental background signal.

Primer Dimer Suppression

Figure 3:
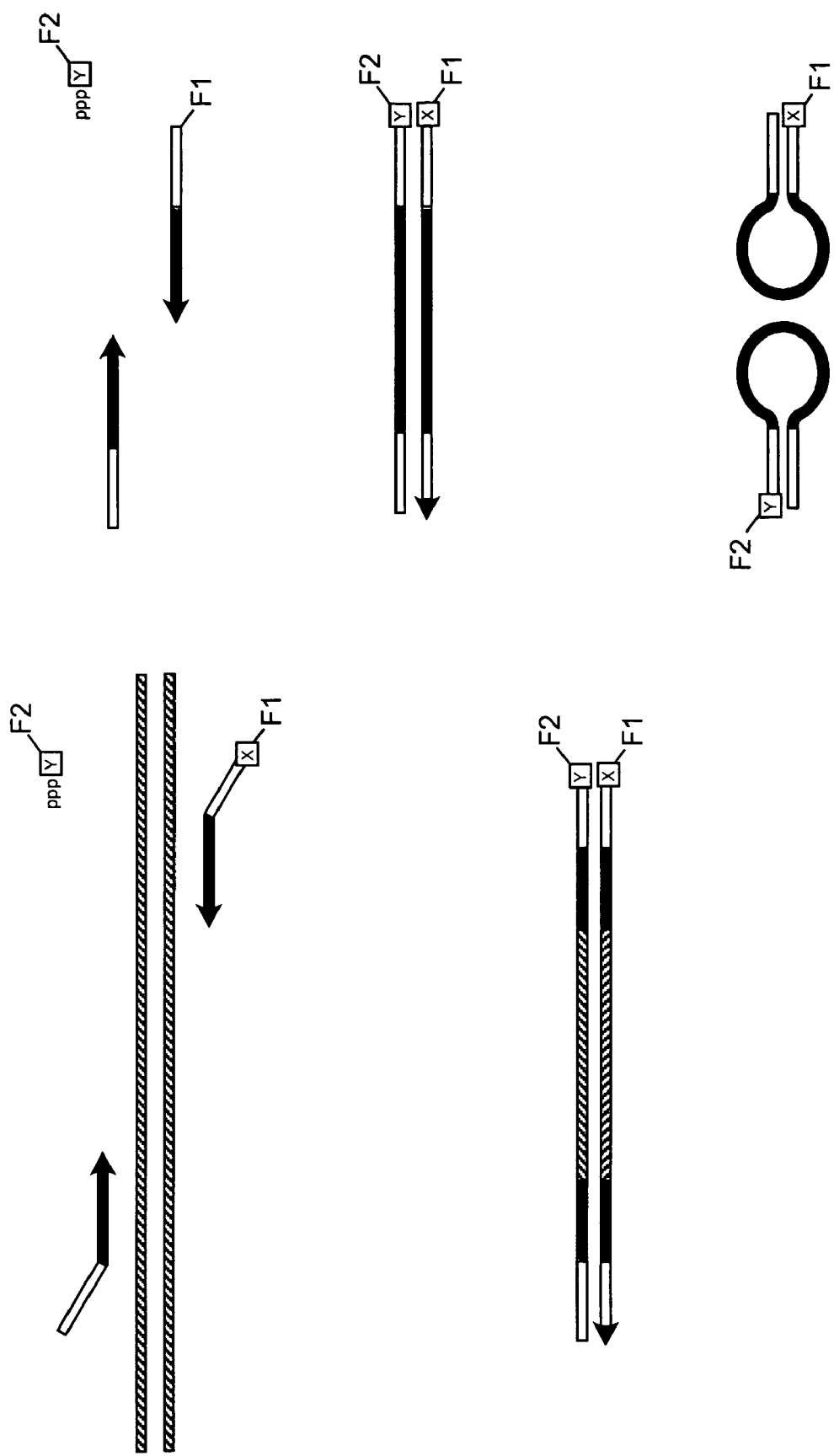
FIG. 3 shows a schematic diagram of one embodiment of the present invention.
Figure 4:
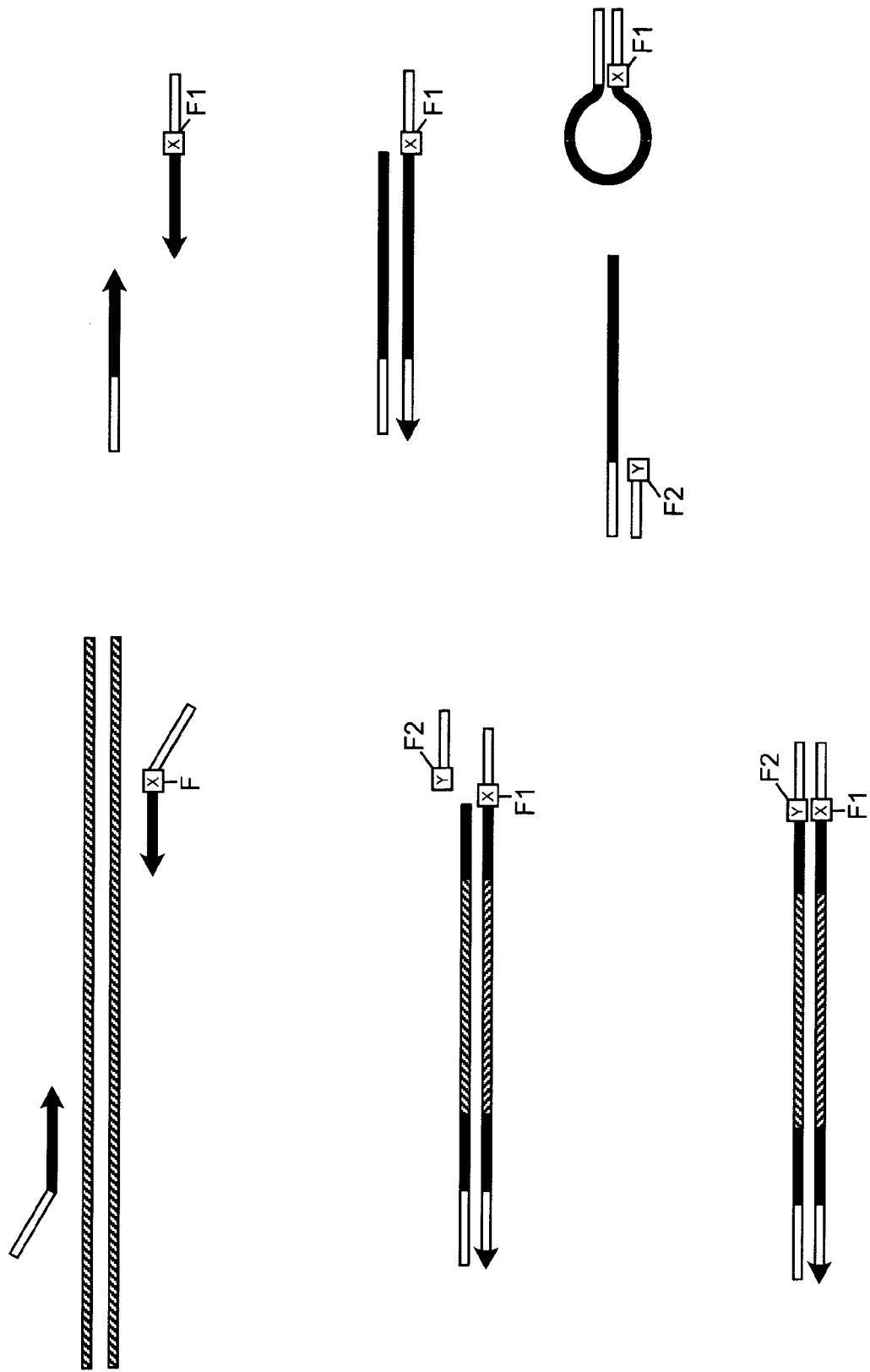
FIG. 4 shows a schematic diagram of one embodiment of the present invention.

In some embodiments, the present invention provides improved methods of suppressing background signal from "primer-dimer" formation in polymerase chain reactions. As described above, in some embodiments, the accumulation of PCR product may be monitored by quenching the signal of a label on the second primer by site-specific incorporation of a nucleotide triphosphate across the DNA duplex at a position near the label of the second primer. In some embodiments, labeled nucleoside triphosphate is incorporated into the elongating first primer during PCR extension. The label on the labeled nucleoside triphosphate is capable of quenching the label on the second oligonucleotide primer (see, e.g., FIGS. 1 and 2). In an alternative embodiment, fluorescence energy transfer (FRET) can be observed between the label of the second oligonucleotide primer (donor dye) and a label on the nucleotide (acceptor dye) (see, e.g., FIGS. 3 and 4). Detection of PCR product can be observed by exciting the donor dye and reading the emission of the incorporated acceptor dye. In yet other alternatives, the second primer may be labeled with an acceptor dye and the label on the nucleotide to be incorporated may be a donor dye. In any of these embodiments, non-specific amplification products also result in the incorporation of a labeled non-natural nucleotide as the complement to the non-natural nucleotide in the second primer. Thus, non-specific amplification products can result in label quenching or energy transfer that can be difficult to distinguish from the intended signal. This problem can be especially acute with non-specific products termed "primer-dimer" products, wherein the PCR primers create a small amplicon that consists essentially of the two primer sequences. These small amplification products tend to amplify very efficiently and can even become the dominant product in a reaction under certain conditions.

The present invention provides methods and compositions to improve the sensitivity of PCR detection using labeled non-natural nucleotides by both suppressing formation of primer-dimer and other non-specific amplification products, and by reducing the signal effect of any such products that do form during a reaction. In preferred embodiments, the present invention provides primers that provide an inhibitory effect on the formation of primer-dimer and other small amplification products. It has been shown that when primers have regions of homology that are incorporated into a duplex fragment via PCR, each resulting strand of the PCR duplex comprises a pair of complementary regions that can, if the PCR strands are separated, anneal to each other to form a stem and loop or "panhandle" structure. Because the complementary regions are introduced by the primers, e.g., in the form of tails comprising "tag" sequences, the formation of the panhandle structure involves annealing of the primer-binding sites, and thus it inhibits further amplification by blocking the annealing of new primers. The local concentration of the complementary sequence provided from the opposite end of a stand is much higher than the concentration of the complementary primers and thus the other end of the stand can occupy the primer binding site before a primer has a chance to anneal. For a very short duplex such as a primer-dimer product, the panhandle structure formation can dramatically reduce amplification of the primer-dimer product.

In a standard labeling system (i.e., using non-interactive labels), any primer-dimer product that does form can be detected, even if the signal is significantly reduced. Using the interactive labels described above, however, the panhandle formation is useful not just in suppressing further amplification of the primer-dimer product, but also in reducing detectable signal from any such amplicon that forms. One embodiment is diagrammed in FIG. 1. The left side of this figure shows one embodiment of the detection method described above, wherein a non-natural nucleotide comprising a quencher moiety is incorporated into a PCR product opposite a non-natural nucleotide having a fluorescent label. In this embodiment, the PCR primers comprise a 5' tail region that is not complementary to the target nucleic acid, and each primer has the same 5' tail sequence. Upon amplification, the 5' tail region of each primer serves as template for the formation of the complementary sequence on the 3' end of each completed strand. When the intended target is amplified, the product is long enough that the complementary regions on the ends of each strand provide insignificant interference with subsequent primer binding.

The right side of FIG. 1 diagrams the formation of a primer-dimer product using the same primers. The short product having complementary ends easily forms a panhandle structure that inhibits further amplification. Nonetheless, any amplification that does occur does incorporate the label-quencher pair. However, upon heating and cooling, these product again form the panhandle structure. Formation of this structure effectively separates the dye and quencher moieties, thus making the panhandle products invisible to the detection system that detects only their proximity.

In some embodiments, initial target specific priming occurs using primers that each comprise a non-target tail comprising a "tag" sequence, wherein the tag sequence is incorporated into amplification products. Further amplification is carried out using tag primers. The sequence of the tag primer is conveniently identical to the sequence of the tag sequence in the tails of the initial primers. The tag primer preferably comprises a sequence capable of hybridization to all tag sequences. All tag sequences are preferably identical. It will be appreciated that minor changes may be made to the sequence of the tag primer without affecting its performance to any significant extent.

Tailed primers can be used to prevent the formation of primer-dimers and other inter-primer artifacts. While not being limited to any particular mechanism, it is believed that the formation of primer dimers is dependent on some degree of homology between primers and their use at high concentrations. It may be possible to reduce the formation of primer dimers by careful primer design. However where many primers are used at high concentrations, for example in PCR multiplexes, this becomes more difficult. With the use of tag primers, the target-specific diagnostic primers may be used at concentrations that allow satisfactory priming on their genomic template(s) but do not allow significant PCR amplification or primer-dimer formation. In addition, the presence of complementary sequences on the ends of the short primer-dimer strands that do form cause these strands to preferentially fold on themselves to inhibit further amplification. See, e.g., U.S. Pat. No. 5,565,340 to Chenchik, et al., U.S. Pat. No. 6,270,967 to Whitcombe, et al., and Brownie, et al., Nucleic Acids Res. 25(16): 3235-41 (1997), each of which is incorporated herein by reference. Tag primers are easily adapted for use with the non-natural nucleotide compositions and methods of the present invention.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A kit comprising a dideoxy iso-G nucleotide.
2. The kit of claim 1, further comprising a oligonucleotide primer.
3. The kit of claim 1, further comprising a polymerase.
4. The kit of claim 3, wherein said polymerase is a DNA polymerase.
5. The kit of claim 4, wherein said DNA polymerase is a thermostable polymerase.
6. The kit of claim 5, wherein said thermostable polymerase lacks 5'-nuclease activity.
7. The kit of claim 1, further comprising reagents for conducting a polymerase chain reaction.
8. A method for analyzing a target nucleic acid, comprising: exposing a target nucleic acid to polymerase, a first amplification primer having a first non-natural nucleotide, a second amplification primer, and an extension disabled second non-natural nucleotide complementary to said first non-natural nucleotide under conditions such that an extension product is generated from at least said second amplification primer, wherein said extension product incorporates said second non-natural nucleotides and analyzing said target nucleic acid by detecting said extension product.
9. The method of claim 8, wherein said first and second amplification primers are selected to hybridize to a portion of said target nucleic acid to define an amplification region, wherein said amplification region is selected to minimize the presence of T nucleotides in said amplification region.
10. A method for analyzing a target nucleic acid using non-natural nucleotides, comprising:
  a) providing:
    i) a first non-natural nucleotide;
    ii) a sample suspected of comprising a target nucleic acid;
    iii) a first amplification primer having a second non-natural nucleotide, said primer having a sequence selected to be upstream of a region of said target nucleic acid to be amplified, wherein said region is selected to avoid or minimize the presence of natural nucleotides that can base-pair with said first non-natural nucleotide;
    iv) a second amplification primer; and
    v) apolymerase;
  b) exposing said sample to said first non-natural nucleotide, said first and second amplification primers, and said polymerase under condition an extension product is generated from at least said second amplification primer, wherein said extension product incorporates at least one said first non-natural nucleotide; and
  c) analyzing said target nucleic acid by detecting said extension product.
11. The method of claim 10, wherein said first non-natural nucleotide is iso-G.
12. The method of claim 10, wherein said natural nucleotides comprise thymidine.
13. The method of claim 10, further comprising the step of detecting the presence or absence of said target nucleic acid in said sample.
14. The method of claim 10, wherein said region does not contain said natural nucleotides in 20 bases upstream of said first amplification primer.
15. The method of claim 10, wherein said region does not contain said natural nucleotides in 10 bases upstream of said first amplification primer.
16. The method of claim 10, wherein said region does not contain said natural nucleotides in 5 bases upstream of said first amplification primer.
17. The method of claim 10, wherein said first non-natural nucleotide comprises an extension disabled non-naturally occurring nucleotide.
18. The method of claim 10, wherein said region is selected by the use of a processor configured to analyze a sequence characteristic of said region selected from the group consisting of: location of said natural bases in said region, number of said natural bases in said region, and presence of said natural bases in said region.
19. A method for detecting a target nucleic acid, comprising:
  a) contacting the sample with a polymerase; a first oligonucleotide primer comprising a 3' region complementary to a first portion of the target nucleic acid and a 5' region comprising a tag sequence; a second oligonucleotide primer comprising a 3' region comprising a sequence complementary to a second portion of the target nucleic acid, a 5' region comprising the tag sequence, and a 5' terminal region comprising a non-natural base;

b) conducting a polymerase chain reaction to produce an amplified sample under conditions wherein the target nucleic acid, if present in the sample, is amplified using the first and second oligonucleotide primers to generate amplification products comprising a target amplification product having (i) a double-stranded region and (ii) a single-stranded region that comprises the non-natural base, c) contacting said amplified sample with a reporter comprising a label and a non-natural base that is complementary to the non-natural base of the single-stranded region;

d) incorporating the reporter into the amplification product opposite the non-natural base of the single-stranded region; and e) detecting the incorporation of the reporter; wherein the detection of the incorporation of the reporter correlates with presence of the target nucleic acid in the sample.

20. The method of claim 19, further comprising step e) treating the amplified sample under conditions wherein non-target amplification product consisting essentially of primer-dimer product is treated to separate the strands, wherein each separated strand forms a duplex region comprising a tag sequence and a region that is complementary to the tag sequence.

21. The method of claim 19, wherein each of said second oligonucleotide primer and said reporter comprise interactive labels.

22. The method of claim 21, wherein said interactive labels comprise a fluorophore.

23. The method of claim 21 wherein said interactive labels comprise a quencher.

24. The method of claim 21, wherein said second oligonucleotide primer comprises a fluorophore and said reporter comprises a quencher.

25. The method of claim 21, wherein said second oligonucleotide primer comprises a quencher and said reporter comprises a fluorophore.

26. The method of claim 21, wherein said second oligonucleotide primer comprises a first fluorophore and said reporter comprises a second fluorophore.

27. The method of claim 19, wherein the step of contacting the sample with a reporter comprises contacting the sample with a reporter comprising a label and a nucleoside triphosphate of a non-natural base that is complementary to the non-natural base of the single-stranded region.

28. The method of claim 19, wherein the step of contacting the sample with a reporter comprises contacting the sample with a reporter consisting essentially of a label and a nucleoside triphosphate of a non-natural base that is complementary to the non-natural base of the single-stranded region.

29. The method of claim 19, wherein the incorporating step comprises incorporating the reporter into the amplification product opposite the non-natural base of the single-stranded region using a nucleic acid polymerase.

30. The method of claim 19, wherein the incorporating step comprises incorporating the reporter into the amplification product opposite the non-natural base of the single-stranded region using a ligase.

31. A kit comprising: a first oligonucleotide primer comprising a 3' region complementary to a first portion of the target nucleic acid and a 5' region comprising a tag sequence, a second oligonucleotide primer comprising a 3' region comprising a sequence complementary to a second portion of the target nucleic acid, a 5' region comprising the tag sequence, and a 5' terminal region comprising a non-natural base; and a reporter comprising a label and a non-natural base that is complementary to the non-natural base in said second oligonucleotide primer.

32. The kit of claim 31, further comprising a third oligonucleotide primer comprising a 3' portion consisting essentially of said tag sequence.

33. The kit of claim 31, wherein the reporter comprises an oligonucleotide comprising the non-natural base.

34. The kit of claim 31, wherein the reporter does not include any base other than the non-natural base.

35. The kit of claim 31, wherein the second region of the second oligonucleotide primer further comprises a label and the labels of the reporter and the second region of the second oligonucleotide primer comprise a pair of fluorophores where the emission of one of the fluorophores stimulates the emission of the other fluorophore.

36. The kit of claim 31, wherein the second region of the second oligonucleotide primer further comprises a label and the labels of the reporter and the second region of the second oligonucleotide primer comprise a signal generating element and a signal quenching element.

37. The kit of claim 31, further comprising a polymerase.

* * * * *